(12) United States Patent
Kaplan et al.

(10) Patent No.: US 10,889,421 B2
(45) Date of Patent: Jan. 12, 2021

(54) UNIVERSAL STERILE PACKAGING ASSEMBLY

(71) Applicant: Stryker European Holdings I, LLC, Kalamazoo, MI (US)

(72) Inventors: Rufina Kaplan, Highland Mills, NY (US); Orrin R. Levine, Wyckoff, NJ (US); Charles L. Bush, Jr., Wayne, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 371 days.

(21) Appl. No.: 15/377,202

(22) Filed: Dec. 13, 2016

(65) Prior Publication Data

US 2017/0166377 A1    Jun. 15, 2017

Related U.S. Application Data

(60) Provisional application No. 62/267,022, filed on Dec. 14, 2015.

(51) Int. Cl.
| | | |
|---|---|---|
| *B65D 75/36* | (2006.01) | |
| *A61B 17/86* | (2006.01) | |
| *A61B 50/30* | (2016.01) | |
| *A61F 2/00* | (2006.01) | |
| *B65D 75/52* | (2006.01) | |
| *A61B 50/20* | (2016.01) | |

(Continued)

(52) U.S. Cl.
CPC .......... *B65D 75/366* (2013.01); *A61B 17/865* (2013.01); *A61B 50/30* (2016.02); *A61F 2/0095* (2013.01); *B65D 75/52* (2013.01); *A61B 17/70* (2013.01); *A61B 17/80* (2013.01); *A61B 17/86* (2013.01); *A61B 50/20* (2016.02); *A61B 2050/0065* (2016.02); *A61B 2050/314* (2016.02)

(58) Field of Classification Search
CPC .......... A61B 2050/3006; B65D 75/366; B65D 75/32; B65D 75/38; B65B 69/00
USPC .................................. 53/492, 381.1, 381.4
See application file for complete search history.

(56) References Cited

U.S. PATENT DOCUMENTS

| 2,846,806 | A | | 8/1958 | Gaines | |
|---|---|---|---|---|---|
| 3,376,973 | A | * | 4/1968 | Granowitz | ....... A61B 17/06123 |
| | | | | | 206/63.3 |

(Continued)

FOREIGN PATENT DOCUMENTS

| WO | 03079918 A1 | 10/2003 |
|---|---|---|
| WO | 2005016183 A1 | 2/2005 |

OTHER PUBLICATIONS

The Partial European Search Report for EP Application No. 16203879.8 dated Apr. 20, 2017.

*Primary Examiner* — Anna K Kinsaul
*Assistant Examiner* — Daniel Jeremy Leeds
(74) *Attorney, Agent, or Firm* — Lerner, David, Littenberg, Krumholz & Mentlik, LLP

(57) ABSTRACT

A universal sterile packaging assembly for an orthopedic device includes an outer blister having a first recessed central region and an inner blister having a second recessed central region. The second recessed central region includes a protrusion configured for securement of a medical part thereto. The inner blister is sized to fit within the first recessed central region. The assembly also includes a first lid securable to the inner blister and a second lid securable to the outer blister so as to enclose the inner blister within the outer blister.

17 Claims, 6 Drawing Sheets

(51) Int. Cl.
*A61B 50/00* (2016.01)
*A61B 17/70* (2006.01)
*A61B 17/80* (2006.01)

(56) References Cited

U.S. PATENT DOCUMENTS

| | | | |
|---|---|---|---|
| 3,444,994 A * | 5/1969 | Kaepernik | A61B 17/06138 |
| | | | 206/63.3 |
| 3,554,429 A | 1/1971 | Cohen | |
| 3,613,879 A * | 10/1971 | Kemble | A61B 17/06133 |
| | | | 206/210 |
| 3,616,898 A * | 11/1971 | Massie | B65D 75/30 |
| | | | 116/207 |
| 3,759,376 A * | 9/1973 | Lisowski | A61B 17/06138 |
| | | | 206/388 |
| 3,972,418 A * | 8/1976 | Schuler | A61B 17/06133 |
| | | | 206/63.3 |
| 4,111,302 A | 9/1978 | Roth | |
| 4,142,632 A | 3/1979 | Sandel | |
| 4,324,331 A | 4/1982 | Ignasiak | |
| 4,482,053 A * | 11/1984 | Alpern | A61L 2/26 |
| | | | 206/439 |
| 4,511,035 A * | 4/1985 | Alpern | A61B 17/0682 |
| | | | 206/339 |
| 4,602,715 A | 7/1986 | Sarver et al. | |
| 4,708,241 A * | 11/1987 | Black | A61B 17/06138 |
| | | | 206/227 |
| 4,782,942 A | 11/1988 | Ashley et al. | |
| 4,842,141 A | 6/1989 | Segal | |
| 4,850,477 A | 7/1989 | Gelardi et al. | |
| 4,903,827 A | 2/1990 | Phelps et al. | |
| 4,945,710 A | 8/1990 | Hustad | |
| 4,978,510 A | 12/1990 | Smith | |
| 4,986,414 A | 1/1991 | Ashley et al. | |
| D315,868 S | 4/1991 | Gelardi et al. | |
| 5,076,431 A * | 12/1991 | Thompson | A61B 50/30 |
| | | | 206/347 |
| D326,409 S | 5/1992 | Krueger et al. | |
| 5,123,528 A * | 6/1992 | Brown | A61B 17/06138 |
| | | | 206/63.3 |
| 5,129,511 A * | 7/1992 | Brown | A61B 17/06138 |
| | | | 206/339 |
| 5,133,454 A | 7/1992 | Hammer | |
| 5,176,258 A * | 1/1993 | Antal | B65D 75/326 |
| | | | 206/438 |
| 5,246,109 A | 9/1993 | Markle et al. | |
| 5,277,299 A * | 1/1994 | Holzwarth | A61B 17/06138 |
| | | | 206/380 |
| 5,341,934 A | 8/1994 | Hsu | |
| 5,353,922 A * | 10/1994 | Sinn | A61B 17/06133 |
| | | | 206/380 |
| 5,368,160 A * | 11/1994 | Leuschen | A61C 8/0087 |
| | | | 206/339 |
| 5,379,895 A | 1/1995 | Foslien | |
| 5,388,701 A | 2/1995 | Ridgeway | |
| 5,392,903 A * | 2/1995 | Sinn | A61B 17/06123 |
| | | | 206/394 |
| 5,392,917 A * | 2/1995 | Alpern | B65D 77/2056 |
| | | | 206/370 |
| 5,405,000 A * | 4/1995 | Hagedon | B65D 81/075 |
| | | | 206/216 |
| 5,405,005 A | 4/1995 | White | |
| 5,441,150 A | 8/1995 | Ma | |
| 5,447,234 A | 9/1995 | Faulstick et al. | |
| 5,497,601 A | 3/1996 | Gonzalez | |
| 5,562,208 A | 10/1996 | Hasler et al. | |
| 5,590,778 A | 1/1997 | Dutchik | |
| 5,669,501 A | 9/1997 | Hissong et al. | |
| 5,685,429 A | 11/1997 | Myers | |
| 5,690,222 A * | 11/1997 | Peters | B65D 75/32 |
| | | | 206/339 |
| 5,772,025 A | 6/1998 | Chen et al. | |
| 6,182,480 B1 * | 2/2001 | Kim | E05B 73/0023 |
| | | | 206/1.5 |
| 6,622,864 B1 * | 9/2003 | Debbs | A61L 2/26 |
| | | | 206/363 |
| 6,783,004 B1 | 8/2004 | Rinner | |
| 6,814,236 B2 | 11/2004 | Roshdy | |
| 6,827,212 B2 | 12/2004 | Reaux | |
| 6,830,149 B2 * | 12/2004 | Merboth | A01N 1/02 |
| | | | 206/438 |
| 6,843,374 B1 | 1/2005 | Li et al. | |
| 6,889,839 B1 * | 5/2005 | Rosten | B65D 81/075 |
| | | | 206/363 |
| 6,915,901 B2 * | 7/2005 | Feinberg | A61B 17/00491 |
| | | | 206/363 |
| 6,994,213 B2 | 2/2006 | Giard, Jr. et al. | |
| 7,066,329 B2 | 6/2006 | Riley | |
| 7,270,235 B2 | 9/2007 | Chen | |
| 7,475,776 B2 | 1/2009 | Detruit et al. | |
| 7,650,991 B2 * | 1/2010 | Hester | B25B 23/00 |
| | | | 206/339 |
| 7,770,728 B2 | 8/2010 | Kærn | |
| 7,832,560 B2 * | 11/2010 | Tilton | B65D 73/0092 |
| | | | 206/459.5 |
| 7,931,143 B1 | 4/2011 | Lin | |
| 8,006,839 B2 * | 8/2011 | Hafner | A61F 2/0095 |
| | | | 206/363 |
| 8,079,468 B2 | 12/2011 | Pleil et al. | |
| 8,096,420 B2 | 1/2012 | Marhsall et al. | |
| 8,112,973 B2 * | 2/2012 | Fischer | A61B 17/06114 |
| | | | 53/111 R |
| 8,113,348 B2 | 2/2012 | Foster | |
| 8,177,066 B2 * | 5/2012 | Tilton | B65D 73/0057 |
| | | | 206/462 |
| 8,240,468 B2 * | 8/2012 | Wilkinson | A61B 5/417 |
| | | | 206/363 |
| 8,403,941 B2 | 3/2013 | Peterson et al. | |
| 8,413,811 B1 | 4/2013 | Arendt | |
| 8,496,690 B2 | 7/2013 | Sixto et al. | |
| 8,511,473 B1 | 8/2013 | Bontrager et al. | |
| 8,518,341 B2 | 8/2013 | Friderich et al. | |
| 8,584,853 B2 | 11/2013 | Knight et al. | |
| 8,701,890 B2 | 4/2014 | Bertazzoni et al. | |
| 8,701,891 B2 | 4/2014 | Bontrager et al. | |
| D712,279 S | 9/2014 | Akana et al. | |
| 9,017,851 B2 | 4/2015 | Felder et al. | |
| 9,095,848 B2 | 8/2015 | Carrel et al. | |
| 9,101,349 B2 | 8/2015 | Knight et al. | |
| D752,430 S | 3/2016 | Stevenson et al. | |
| 9,687,300 B2 | 6/2017 | Hartfelder et al. | |
| 9,707,039 B2 * | 7/2017 | Grabowski | B65D 73/0092 |
| 10,086,131 B2 * | 10/2018 | Okihara | B65D 77/2024 |
| 10,245,025 B2 * | 4/2019 | Prikril | A61B 17/06133 |
| 2002/0112981 A1 | 8/2002 | Cooper et al. | |
| 2002/0125158 A1 | 9/2002 | High et al. | |
| 2003/0121810 A1 * | 7/2003 | Roshdy | B65D 1/36 |
| | | | 206/363 |
| 2005/0017059 A1 * | 1/2005 | Salani | A61F 15/001 |
| | | | 229/72 |
| 2005/0033430 A1 | 2/2005 | Powers et al. | |
| 2005/0173278 A1 | 8/2005 | Caron | |
| 2005/0241974 A1 | 11/2005 | Chen | |
| 2006/0243616 A1 * | 11/2006 | Caron | A61B 50/30 |
| | | | 206/349 |
| 2007/0034538 A1 * | 2/2007 | Landis | A61F 2/0095 |
| | | | 206/438 |
| 2008/0029419 A1 | 2/2008 | Appelbaum | |
| 2008/0190794 A1 * | 8/2008 | Farrar | E05B 73/0023 |
| | | | 206/308.2 |
| 2008/0283443 A1 | 11/2008 | Green | |
| 2009/0266728 A1 * | 10/2009 | Turner | A61B 17/865 |
| | | | 206/363 |
| 2011/0113437 A1 * | 5/2011 | Day | E05B 73/0023 |
| | | | 720/728 |
| 2011/0186456 A1 | 8/2011 | Bertazzoni et al. | |
| 2011/0288596 A1 | 11/2011 | Brand et al. | |
| 2012/0256748 A1 * | 10/2012 | Russell | E05B 73/0023 |
| | | | 340/572.1 |
| 2013/0233736 A1 * | 9/2013 | Hess | A61F 2/0095 |
| | | | 206/210 |

(56) References Cited

U.S. PATENT DOCUMENTS

| | | | |
|---|---|---|---|
| 2014/0215976 A1* | 8/2014 | Maasarani | A61M 5/002 |
| | | | 53/492 |
| 2014/0360900 A1* | 12/2014 | Mizuoka | B65D 75/30 |
| | | | 206/305 |
| 2015/0021221 A1* | 1/2015 | Hendrickson | A61B 50/20 |
| | | | 206/438 |
| 2016/0101891 A1* | 4/2016 | Bailey | B65D 7/10 |
| | | | 53/492 |
| 2016/0262905 A1* | 9/2016 | Prado | A61F 2/447 |
| 2016/0304260 A1* | 10/2016 | Ahn | B65D 75/366 |
| 2017/0056122 A1* | 3/2017 | Ramsey | B65D 21/0223 |
| 2018/0263721 A1* | 9/2018 | Volk | A61B 50/33 |

* cited by examiner

UNIVERSAL STERILE PACKAGING ASSEMBLY

CROSS-REFERENCE TO RELATED APPLICATION

This application claims the benefit of the filing date of U.S. Provisional Patent Application No. 62/267,022, filed Dec. 14, 2015, the disclosure of which is hereby incorporated herein by reference.

BACKGROUND OF THE INVENTION

Maintaining proper sterilization of medical implants or parts utilized in orthopedic surgery is of paramount importance. Implants or parts that are improperly sterilized or maintained can lead to infections in a patient. These infections can have significant side effects, including some that may require additional surgery. As such, significant efforts are generally undertaken to sterilize and maintain sterilization of medical implants and parts.

In many instances, sterilized implants and/or parts are delivered to the surgical theater in packaging designed to maintain the sterilization. These packages are often in the form of a sealed blister. Typically, the parts are loose or are contained in a smaller package within the sealed blister. In instances where packages are used, however, the packages are not secured to the sealed blister in a manner that ensures the parts remain secured when the package is opened or even during repeated handling. Examples of such packages include those described in U.S. Pat. Nos. 6,889,839, 8,096,420, 8,113,348 and 8,584,853, the disclosures of which are hereby incorporated by reference herein. Such configurations can lead to problems including torn packages and parts falling from the packages when opened. Moreover, because existing sealed blisters do not minimize the risk of parts falling from the package when the seal is removed, existing blisters cannot ensure that parts will not be contaminated. Existing packages also require users to directly contact any parts therein, which can expose them to any sharp edges of the parts when parts are retrieved.

Thus, there exists a need for an improved packaging construct that enhances the safety of handling medical implants or parts.

BRIEF SUMMARY OF THE INVENTION

A first aspect of the present invention is a universal sterile packaging assembly for an orthopedic device. The assembly includes an inner blister having a recessed central region where the recessed central region includes a protrusion adapted to facilitate the securitization of medical parts thereto. A first lid is secured onto the inner blister. The assembly further includes an outer blister that surrounds the inner blister. A second lid is secured onto the outer blister so that both the outer and inner blister are enclosed within.

In another embodiment, the protrusion is two pins adapted to allow a medical part to be hooked onto the pins. In yet another embodiment, the recessed central portion further includes an elevated portion defined by a curved surface, where the protrusion is located on the elevated portion.

In yet another embodiment, the medical part is a plate. The assembly with the plate can further include a separation member adapted to be placed between the plate and the recessed central portion of the inner blister.

In another embodiment, the medical part is a screw. The assembly with the screw can also include a pouch that is configured to store the screw. The pouch is further configured to be attached to the protrusion on the recessed central portion of the inner blister. The pouch can also be adapted to fold in a manner similar to a matchbook.

In a second aspect, the invention relates to an inner blister of a universal sterile packaging assembly for storing and transporting an orthopedic device. The inner blister includes a perimeter region that has a surface with a width extending around an entire perimeter of the inner blister. The inner blister also has an inner region that is central to the perimeter region. The inner region is recessed relative to the perimeter region. On a surface of the inner region, two pins extend in a direction transverse to the surface.

In another embodiment, the inner region further comprises an elevated portion that is located in a middle portion of the inner region. The elevated portion has a convex curved surface relative to the adjacent portions of the inner region surface.

In a third aspect, the invention relates to a method of using a universal sterile packaging assembly. The method includes the steps of opening a first lid attached to an outer blister of the assembly. This is followed by removing an inner blister from the outer blister and transferring the inner blister to a sterile field. Opening a second lid attached to the inner blister follows, and then removing an object secured onto pins of the inner blister.

In another embodiment, the object removed from the pins is a plate and it is removed using a medical instrument. The removal of the pins can be performed by placing clamping prongs of the medical instrument on opposite sides of the object following the opening of the second lid attached to the inner blister.

In yet another embodiment, the object removed from the pins is a pouch and it is removed manually, by hand. Where the pouch is stored in a folded configuration, it can be opened following its removal from the pins in the inner blister. The pouch of this embodiment is foldable in a manner similar to a matchbook.

In another aspect, the invention relates to a universal sterile packaging assembly for an orthopedic device. In one embodiment, the packaging assembly includes an outer blister having a first recessed central region and an inner blister having a second recessed central region including a protrusion configured for securement of a medical part thereto. The inner blister is sized to fit within the first recessed central region. The packaging assembly also includes a first lid securable to the inner blister and a second lid securable to the outer blister so as to enclose the inner blister within the outer blister.

In another embodiment, the protrusion is two pins, and at least one of the pins includes a hook configured so that a medical part is securable thereto. In yet another embodiment, the second recessed central region of the inner blister includes an elevated portion defined by a curved surface. In this embodiment the elevated portion is positioned so that the protrusion extends from the elevated portion. In a variant, the elevated portion is shaped so that the curved surface extends in a convex manner from a surface of the recessed central region external to the elevated portion toward the protrusion.

In one embodiment, the medical part is a plate. In a variant of this embodiment, the assembly includes a separation member configured to be placed between the plate and a surface of the second recessed central region. In another embodiment, the medical part is a screw.

In yet another aspect, the invention relates to a universal sterile packaging assembly for an orthopedic device that includes an inner blister and a pouch. In one embodiment, the assembly includes an inner blister having a perimeter region and an inner region. The perimeter region includes a surface extending around an entire perimeter of the inner blister and the inner region is central to the perimeter region and is recessed relative to the perimeter region. The inner region is partially defined by an inner surface and includes a pin extending in a transverse direction relative to the inner surface of the inner region. The assembly also includes a pouch with an opening corresponding to the pin such that the pouch is releasably securable to the inner blister. In addition, the pouch is configured for the placement of a medical part therein.

In another embodiment, the pouch includes a pocket configured to store the medical part. In a variant, the inner region of the inner blister includes a pin sized and positioned for placement of one or more plates in the inner blister and a pin sized and positioned for placement of one or more pouches in the inner blister.

In yet another embodiment, the pouch is foldable in a manner similar to a matchbook. In a variant, the pouch includes one pocket on each side of the pouch opening so that when the pouch is moved from an open position into a folded position, the respective pockets become closer to one another.

In another aspect, the invention relates to a method of using a universal sterile packaging assembly. In one embodiment, the method includes steps as follows: opening a first lid attached to an outer blister of the assembly; removing an inner blister from the outer blister; transferring the inner blister to a sterile field; opening a second lid attached to the inner blister; and removing an object secured onto a protrusion of the inner blister.

In one embodiment, the object is a plate and removing the plate includes using a medical instrument to remove the plate from the protrusion. In a variant, the method includes an additional step of clamping prongs of the medical instrument to opposite sides of the plate following the opening of the second lid.

In another embodiment, the object is a pouch that includes two parts foldable onto one another. In a variant, removing the pouch includes gripping the pouch and then removing the pouch from its secured position on the inner blister. In another variant, the method includes an additional step of opening the pouch following removal of the pouch from the protrusion. In this step, the opening of the pouch is completed without making any contact with the object disposed within the pouch. In yet another variant, the method includes an additional step of removing the object from within the pouch without making any contact with the object. In another variant, the opening the pouch includes separating the two parts of the pouch so that each part no longer faces the other.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

The present invention is directed to a universal sterile packaging assembly for use in safely storing and transporting medical implants or parts, such as screws and plates. Specifically, the present invention provides two layers of protection against contamination, and thus maintains sterility of medical parts housed thereon in situations such as when the packaging assembly is dropped. In addition, the assembly improves handling, usability and cleanliness. In some variants, the assembly also prevents exposure to the medical parts by a user handling the assembly. In this regard, the assembly is designed to allow access to the medical part without direct touching of same.

Figure 1:
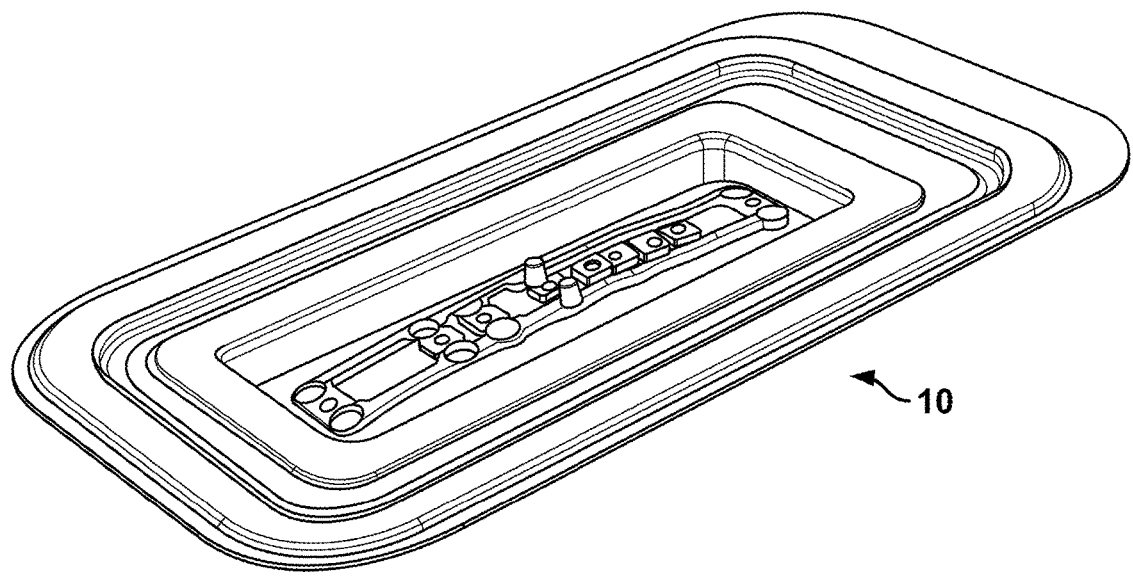
FIG. 1 is a perspective view of a medical device sterile packaging assembly housing a plate, according to one embodiment of the present invention.
Figure 2:
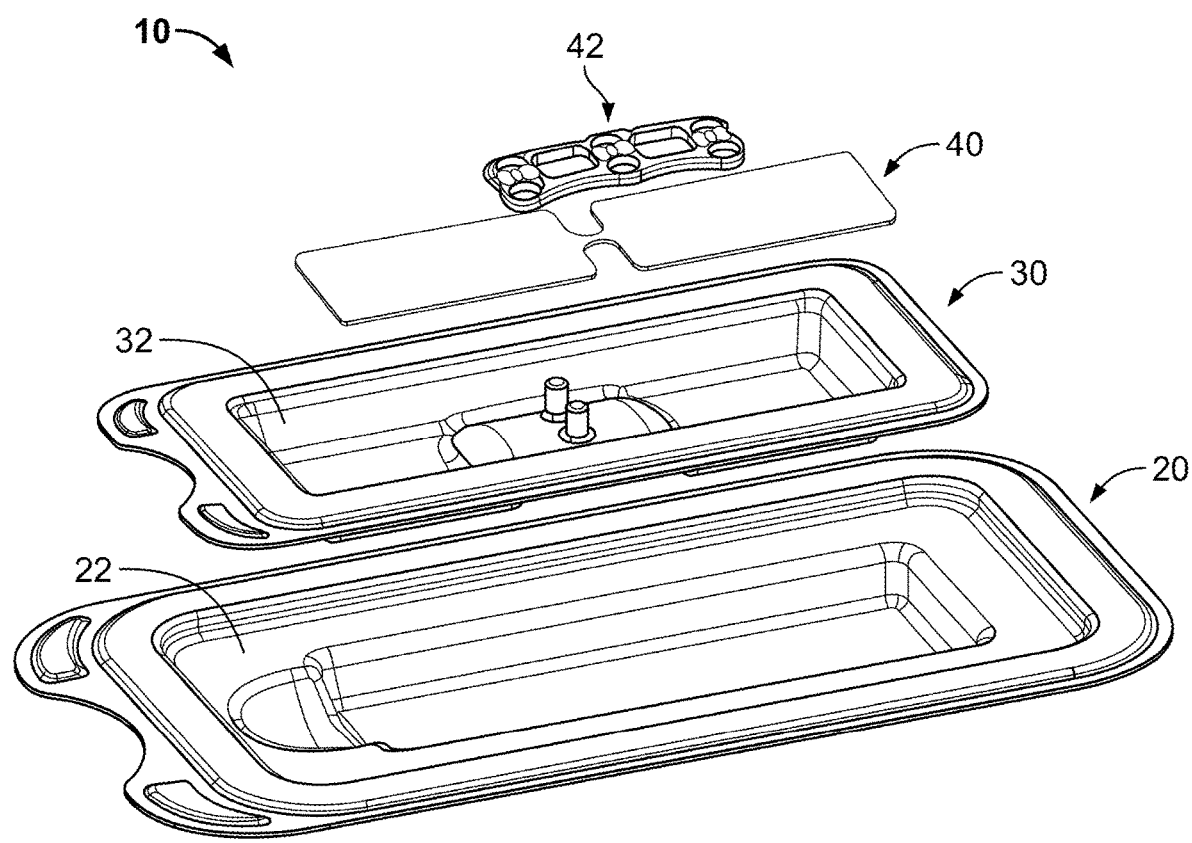
FIG. 2 is an exploded perspective view of the medical device sterile packaging assembly of FIG. 1.

Turning now to the various embodiments of the invention, FIG. 1 depicts a universal sterile packaging assembly 10 with a plate secured to an inner blister. In its protected state, the packaging assembly 10 is sealed by a tyvek lid (not shown). Of course, other seals may be utilized, such as a heat activated lid. FIG. 2 depicts the same assembly, but shows the various elements separated from one another. An outer blister 20 is the largest component, and includes a recess 22 for placement of inner blister 30. Inner blister 30 also includes a recessed central portion 32 that provides space for a separation member 40 to be placed therein and a plate 42 secured over the separation member to the pins of the inner blister 30. As illustrated in FIG. 1, the separation member is shaped to suit a size of the inner blister and the medical parts held within it and is comprised of a material suitable for performance as a barrier between elements that it separates. In addition to the lid on the outer blister, a second lid is sealed onto the inner blister (not shown). In some embodiments, no separation member is included when placing a plate onto the pins of the inner blister. In addition, a separation member can be included in some variants of the other embodiments described herein.

Figure 3:
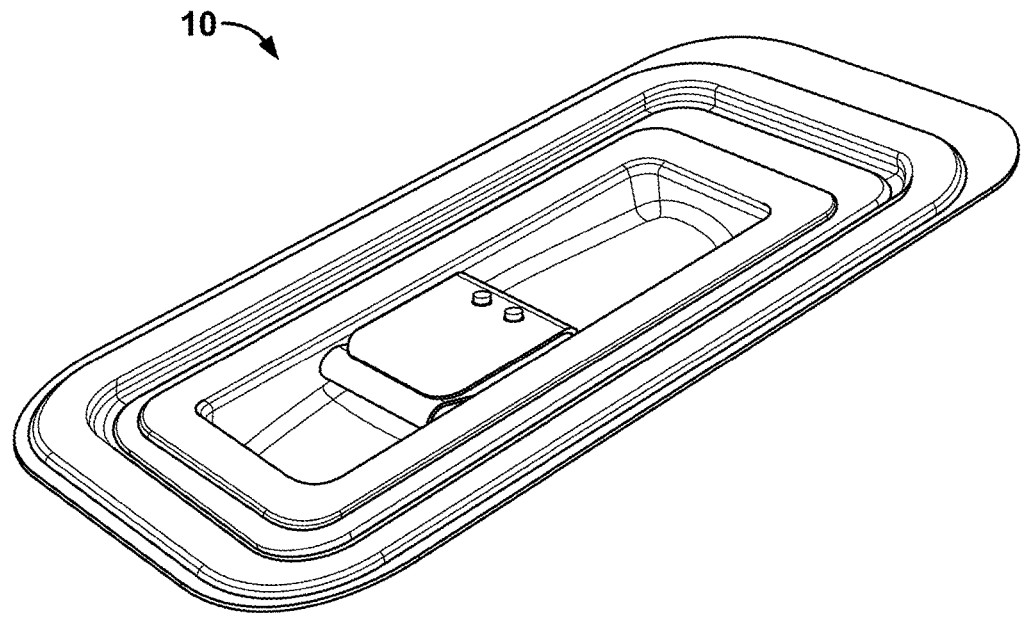
FIG. 3 is a perspective view of the medical device sterile packaging assembly housing a pouch, according to another embodiment of the present invention.
Figure 4:
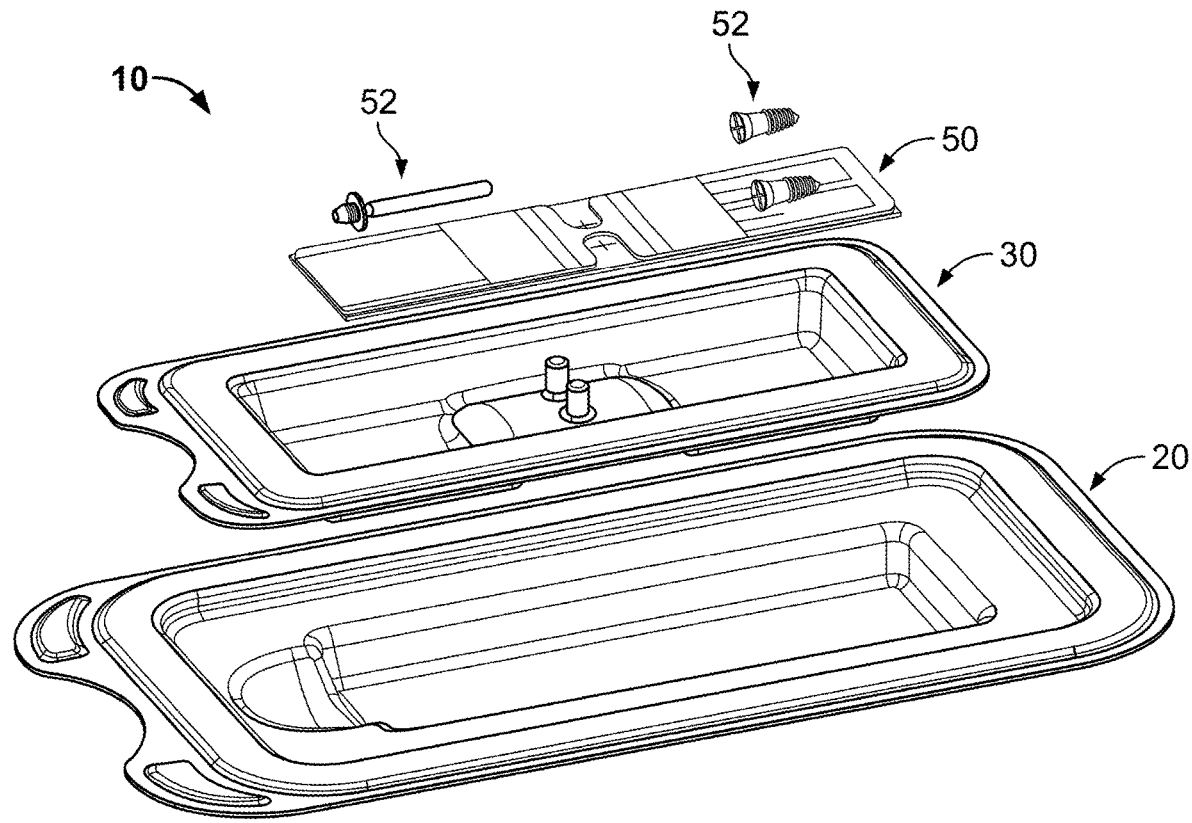
FIG. 4 is an exploded perspective view of the medical device sterile packaging assembly of FIG. 3.

FIGS. 3 and 4 illustrate the same assembly as FIGS. 1 and 2, however, instead of a plate, the inner blister 30 houses a pouch 50. In the embodiment shown, the pouch has the appearance of a matchbook. The pouch includes pockets at each end sized for the storage of screws 52. Each pocket includes a slit for access into the pouch from a central portion of the pouch. In FIG. 3, the pouch is shown in a closed configuration while in FIG. 4 it is in an open configuration. In a variant, the pockets can be sized to accommodate other medical parts such as spacers or rods. In a further variant, the pouch can include a plurality of pockets at each end or pockets at both ends of the pouch. Alternatively, the pouch can include other combinations of pouch size, pocket quantity, pocket size, and other characteristics.

Figure 5A:
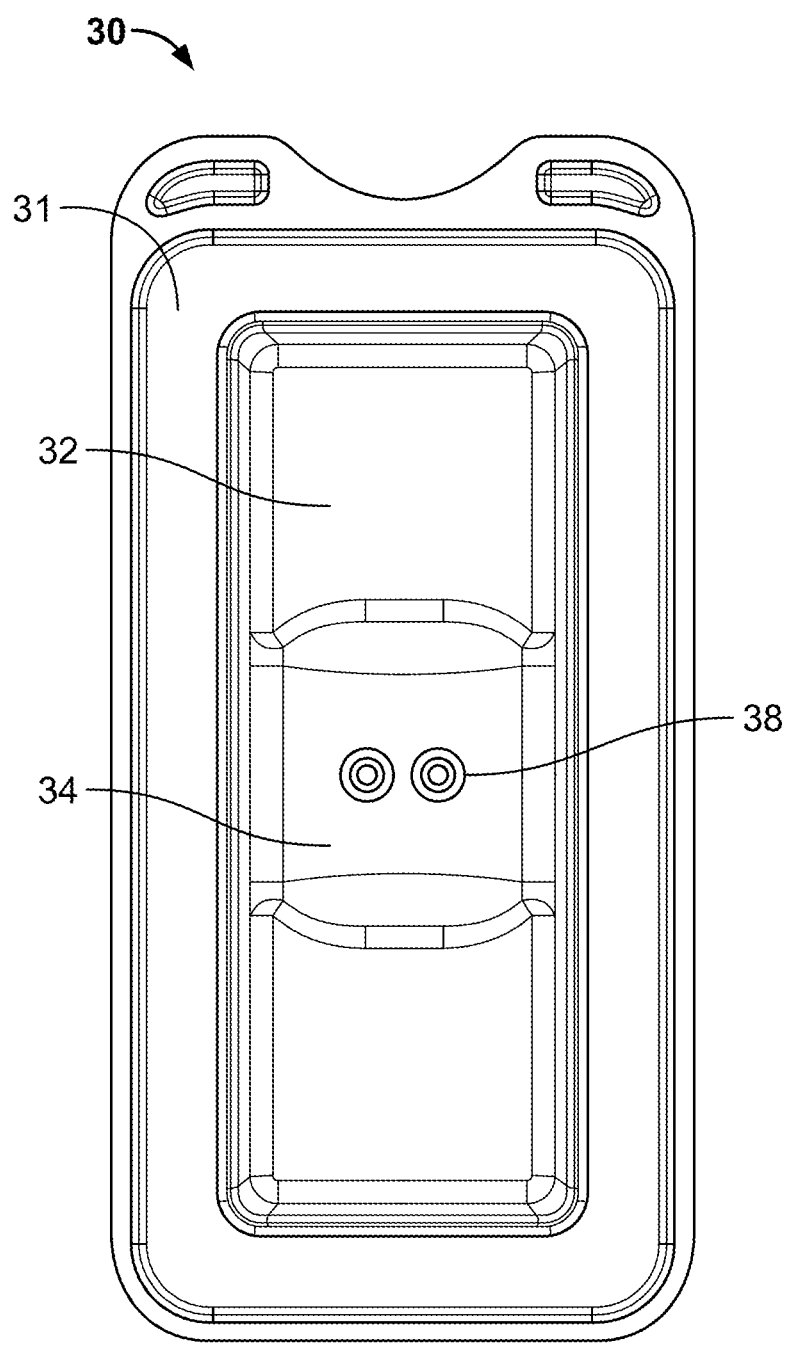
FIGS. 5A, 5B and 5C are a plan view and elevation views of both sides of the inner blister of the medical device sterile packaging assembly of FIG. 1, respectively.
Figure 5B:
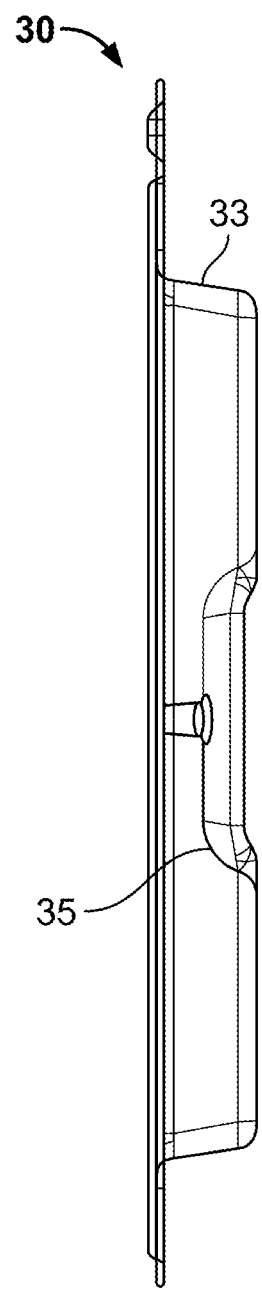
Figure 5C:
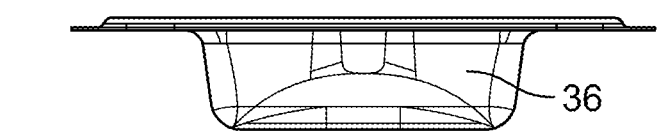

FIG. 5A shows a top down view of the inner blister 30. A perimeter region 31 of the inner blister is characterized by a generally planar surface that extends around a perimeter of the inner blister. Central to the perimeter is an inner region of the inner blister 30 having a cavity 32. Outer walls 33 of the cavity are tapered inward toward a bottom surface of the cavity and the edges between the walls and both the perimeter region and bottom surface are curved. A central portion of the cavity 32 includes an elevated portion 34. The elevated portion 34 is defined by curved surfaces 35, 36 along both a longitudinal axis of the inner blister 30 and an axis transverse to it (best shown in FIGS. 5B and 5C, respectively). On the surface of the elevated portion 34 at approximately a midway point of a length of the inner blister 30 are two pins 38. The pins extend in a direction away from the surface of the inner blister 30 and have circular cross sections. Medical parts can be secured to the pins through features on the pins that allow implants or parts to hook onto them. Of course, the pins may exhibit any shape suitable for holding a medical part. For instance, in another embodiment, the pins can be of an oblong cross-sectional shape. In yet another embodiment, protrusions extend from the surface of the inner region of the inner blister and provide an attachment point between medical parts and the inner blister. As with the pins described above, the protrusions may exhibit any shape suitable for holding a medical part. The top of the protrusions or pins are also part of the seal created by the second lid as movement of the pins is restricted by the lid. This prevents a component of a plate or pouch hooked onto the pins from moving and thus prevents contact between the plate and/or pouch and the second lid in the event that the inner blister is shaken or otherwise transported.

Figure 6:
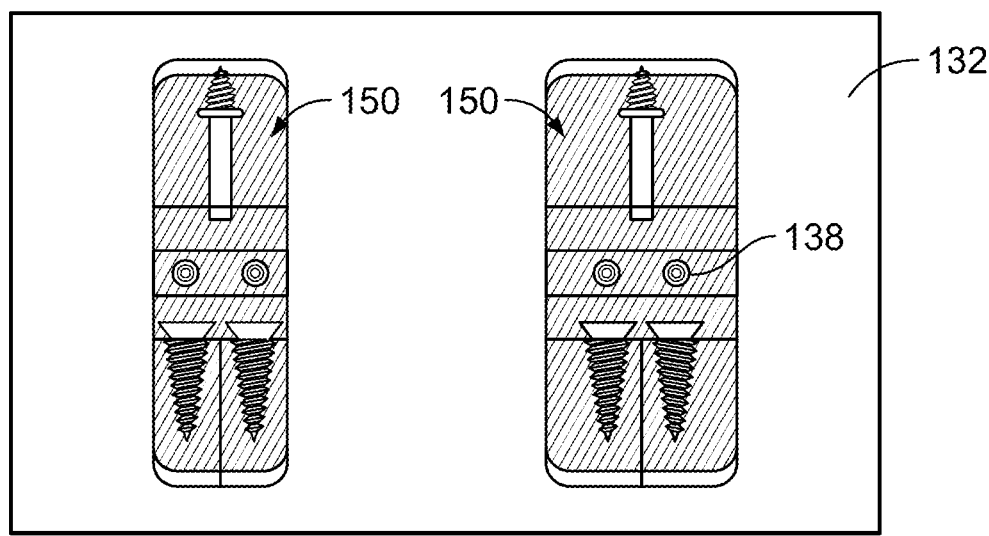
FIG. 6 is another embodiment of the inner blister with four pins.
Figure 7:
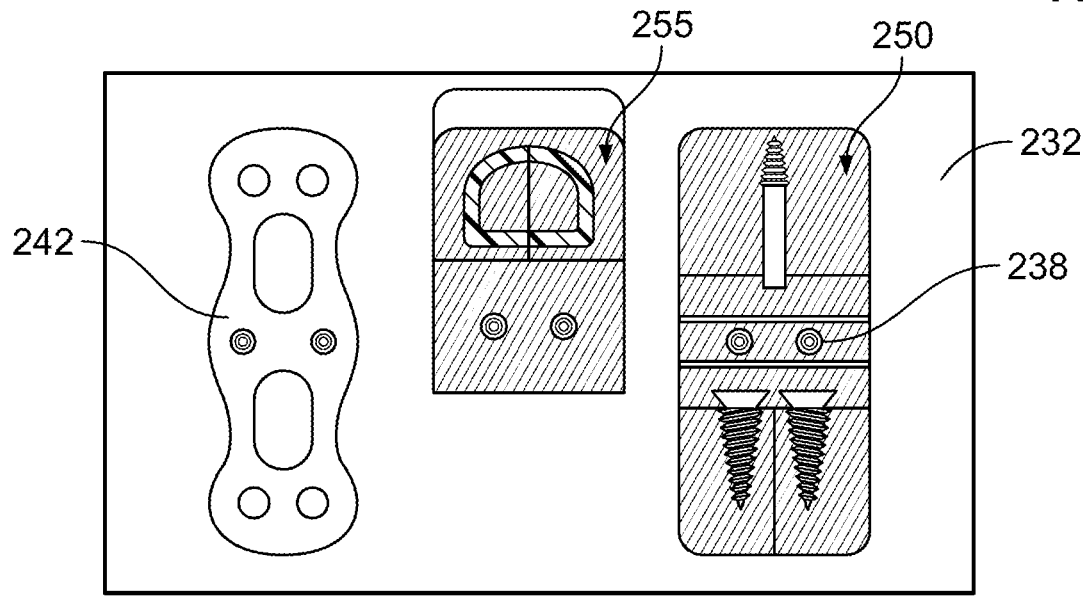
FIG. 7 is yet another embodiment of the inner blister with six pins.
Figure 8:
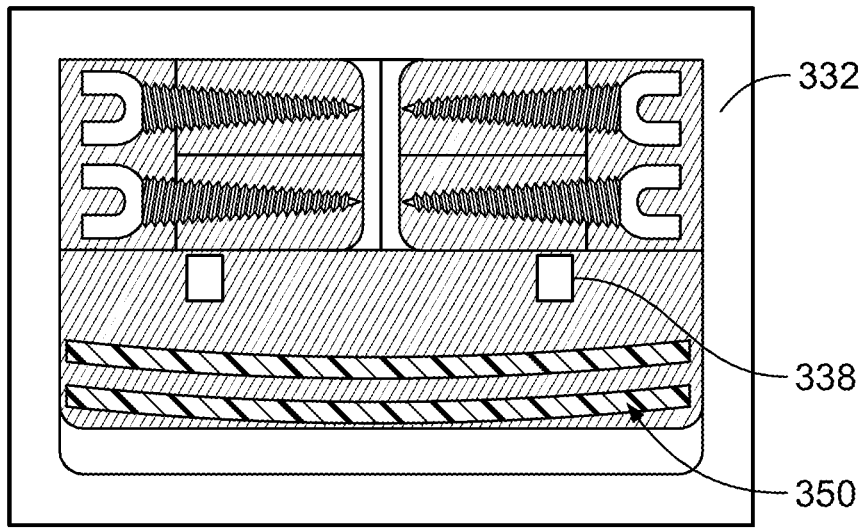
FIG. 8 is one embodiment of the inner blister with two pins.

In still further embodiments, three or more pins can extend from the surface of the inner blister. In the same way, a plurality of protrusions can also be incorporated. The pins can be positioned at various locations on the inner blister. For example, FIG. 6 illustrates a central portion of a cavity 132 of an inner blister with four pins 138 and FIG. 7 illustrates a cavity 232 of an inner blister with six pins 238. In any of the above embodiments, multiple elevated portions can be included to accommodate the placement of pins and/or pouches within the inner blister. In such configurations, multiple pouches can be included. The example of FIG. 6 illustrates the inner blister housing two pouches 150 each holding screws. The pouches shown have the appearance of a matchbook. FIG. 7 illustrates the inner blister housing a cervical plate 242, a pouch holding a PEEK interbody spacer 255, and a pouch holding screws 250. The pouches in FIG. 7 fold in a manner similar to those of FIG. 6 and thus are also like a matchbook. The pouch can also be adapted to hold a variety of medical parts. For example, FIG. 8 illustrates a cavity of an inner blister 332 with two pins 338 housing one pouch 350 containing two rods for pedicle screw fixation and four pedicle screws.

In the embodiment shown in FIGS. 1 and 2, the plate 42 includes at least two openings suitable for placement over pins 38 to secure plate 42 to inner blister 30. Plates of varying size can be used with the assembly. Alternatively, the plate can be placed in or on the separation member, and the separation member itself secured to the pins. In another embodiment, the inner blister, and the separation member where applicable, are shaped to accommodate plates that have curved surfaces.

Figure 9:
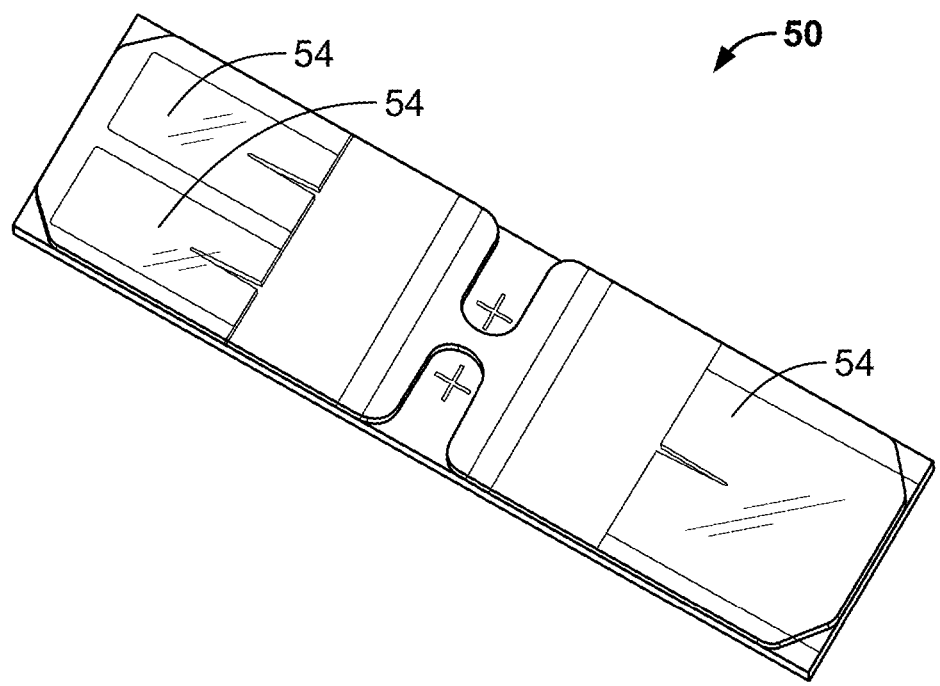
FIG. 9 is a perspective view of the pouch of FIG. 3 in an open configuration.
Figure 10:
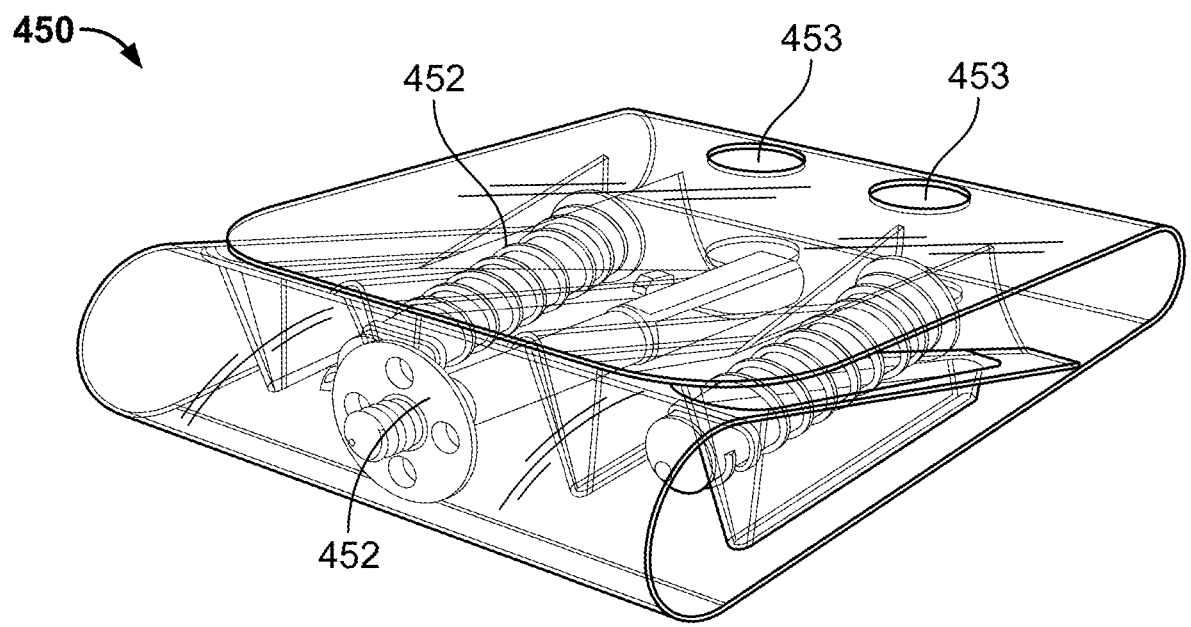
FIG. 10 is a perspective view of another embodiment of the pouch.

In the embodiment shown in FIGS. 3, 4 and 9, the pouch 50 is designed for use with the assembly 10. The pouch includes a flap that is unfolded in a manner similar to a matchbook to change the pouch from a closed to an open configuration. The pouch in the open configuration is shown in FIG. 9, where it can be seen that the pouch includes pockets 54 at each end with slits for placement of medical parts. In another embodiment shown in FIG. 10, the pouch 450 can house at least three screws 452 on one side of the pouch with a two-fold configuration. The pouch of this embodiment also has the appearance of a matchbook. In a variant, the pouch can hold one or two screws, although any number is contemplated. In yet another variant, parts other than screws can be held. Openings 453 are accessible on the closed pouch to hook or otherwise secure the pouch to pins of inner blister. A closed pouch secured to inner blister is shown in FIG. 3. The pouch 50 is opened to retrieve screws 52 or other medical parts. In some embodiments, the pouch is made from a thermoplastic polyurethane material. In other embodiments, the pouch includes a structure that remains in an open configuration when placed in the inner blister and is not folded in any way.

The present invention has numerous advantages. The pin feature within the inner blister ensures that medical parts do not move within the assembly during transport from one location to another. This mitigates any possibility of contamination or alteration to the medical parts. For the same reasons, the risk of a tear in the lid or any other aspect of the assembly during transport is minimized, as is the risk that parts drop or fall out of the inner blister when the assembly is opened to access the parts. Because pins or protrusions are used to secure parts to the assembly and the assembly is sealed, there are at least two levels of protection to ensure safe and sterile transport and handling of medical parts.

Additional advantages include a lower risk of contamination when parts are stored within a pouch. For example, when a pouch is removed from the inner blister, the parts remain within the pouch, thus minimizing the amount of time the parts are exposed to open air prior to use. In addition, the pouch includes a holding area for gripping to ease retrieval of parts from within the pouch when desired, thus reducing the likelihood that a user would need to touch any part. Other advantages of not having to touch any part within a pouch include prevention of incidents where a glove of a user tears. Any tearing of the glove could affect sterility and safety of the user of the parts and/or a patient.

Figure 11:
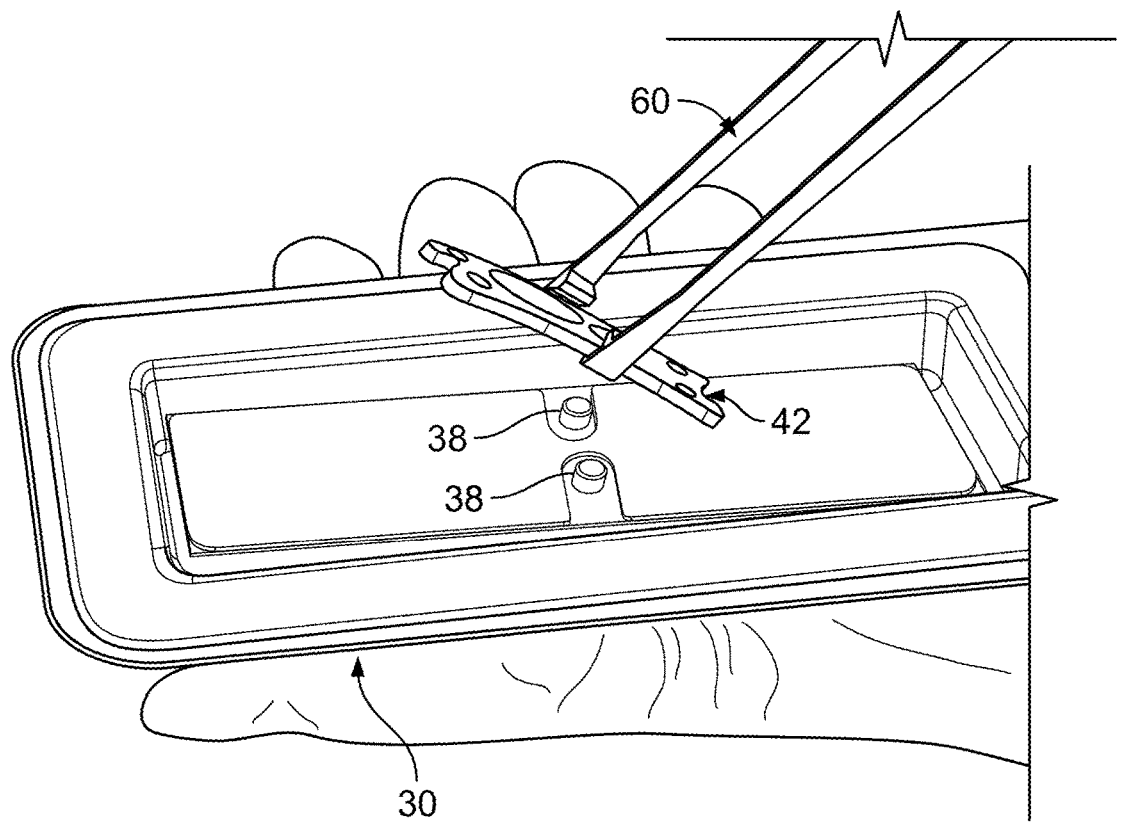
FIG. 11 illustrates a plate being removed from the inner blister of the medical device sterile packaging assembly of FIG. 1.
Figure 12:
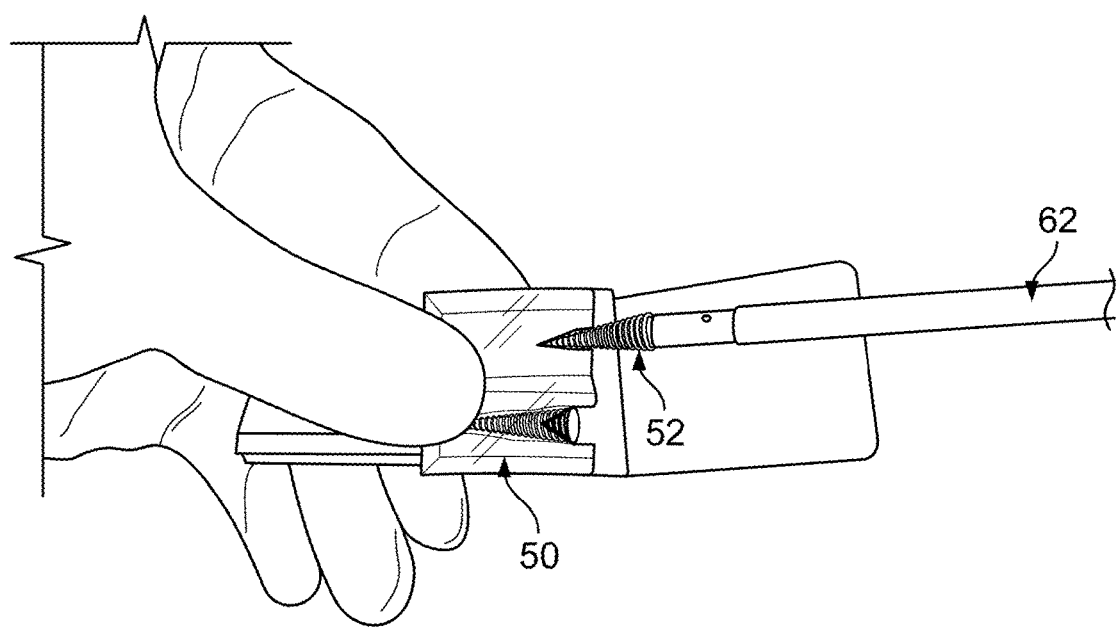
FIG. 12 illustrates a screw being removed from one embodiment of the pouch in the open configuration.

In another aspect, the present invention involves a method of using the universal sterile packaging assembly for storage and transport of medical parts. When all components, including those shown in FIG. 2 or 4, are enclosed and sealed within a tyvek lid, the assembly is in a secure state. A user intent on use of a medical part in a particular sealed assembly will first pick up the assembly by hand. Once the user has reached the location of desired use of the medical part(s), the tyvek lid is removed. With the lid removed, the user transfers the inner blister to a sterile field and then opens it. As indicated above, other lids may be utilized, such as a heat activated lid.

Where the medical part is a plate, the user then obtains a plate holder instrument 60 to remove the plate 42 from the inner blister 30, as shown in FIG. 11. The plate 42 is then ready for use in a desired application. Where the medical part is a screw, the individual first removes the pouch from the inner blister and then opens the pouch 50 placing it in a configuration as shown in FIG. 9. Once the pouch is removed from the inner blister and opened, the user holds the pouch and applies a screw instrument 62 to the screw 52 to remove it from the pouch without making any bodily contact as shown in FIG. 12. The screw is then ready for use in a desired application. In a variant, the user retrieving a pouch does not need to open the pouch as it is stored in an open configuration within the inner blister.

Advantages of the method of the present invention include that the position of the plate or pouch within the inner blister provides easy access and retrieval as it allows a user holding an instrument to reach in to retrieve the part when the assembly is opened. This also ensures that a user will not be required to touch or handle any part(s), and thus the cleanliness and sterility of the part(s) are maintained. Moreover, the user is not exposed to the risk of making contact with any sharp surfaces on the part(s).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A packaging assembly for an orthopedic device comprising:
an outer blister having a first recessed central region;
an inner blister having a second recessed central region including a protrusion, the protrusion configured for securement of a medical part thereto, the inner blister sized to fit within the first recessed central region, the second recessed central region further including an elevated portion defined by a surface convexly curved upwards and away from a bottom surface of the second recessed central portion, the protrusion extending from the elevated portion and away from the bottom surface;
a first lid securable to the inner blister; and
a second lid securable to the outer blister so as to enclose the inner blister within the outer blister,
wherein the protrusion is two pins, at least one of the pins including a hook configured so that a medical part is securable thereto.

2. The packaging assembly of claim 1, wherein the medical part is a plate.

3. The packaging assembly of claim 2, wherein the assembly further comprises a separation member configured to be placed between the plate and a surface of the second recessed central region.

4. The packaging assembly of claim 1, wherein the medical part is a screw.

5. A packaging assembly for an orthopedic device comprising:
an inner blister comprising:
a perimeter region having a surface extending around an entire perimeter of the inner blister; and
an inner region central to the perimeter region, the inner region recessed relative to the perimeter region and partially defined by an inner surface, the inner region further including at least two pins extending in a transverse direction from an elevated portion defined by a surface convexly curved upwards and away from a bottom surface of the second recessed central portion; and
a pouch with an opening corresponding to at least one of the two pins such that the pouch is releasably securable to the inner blister, wherein the pouch is configured for the placement of a medical part therein,
wherein at least one of the pins includes a hook configured so that the medical part is securable thereto.

6. The packaging assembly of claim 5, wherein the pouch includes a pocket configured to store the medical part.

7. The packaging assembly of claim 6, wherein the inner region of the inner blister includes a pin sized and positioned for placement of one or more plates in the inner blister and a pin sized and positioned for placement of one or more pouches in the inner blister.

8. The packaging assembly of claim 5, wherein the pouch is foldable in a manner similar to a matchbook.

9. The packaging assembly of claim 8, wherein the pouch includes one pocket on each side of the opening so that when the pouch is moved from an open position into a folded position, the respective pockets become closer to one another.

10. A method of using a packaging assembly for an orthopedic device comprising:
opening a first lid attached to an outer blister of the assembly;
removing an inner blister from the outer blister;
transferring the inner blister to a sterile field;
opening a second lid attached to the inner blister; and
removing an object secured onto a protrusion extending from an elevated portion of the inner blister, the elevated portion defined by a surface convexly curved upwards and away from a bottom surface of the inner blister, wherein the protrusion is two pins, at least one of the pins including a hook configured so that a medical part is securable thereto.

11. The method of claim 10, wherein the object is a plate and removing the plate further comprises using a medical instrument to remove the plate from the protrusion.

12. The method of claim 11, further comprising a step of clamping prongs of the medical instrument to opposite sides of the plate following the opening of the second lid.

13. The method of claim 10, wherein the object is a pouch that includes two parts foldable onto one another.

14. The method of claim 13, wherein removing the pouch further comprises gripping the pouch and then removing the pouch from its secured position on the inner blister.

15. The method of claim 14, further comprising a step of opening the pouch following removal of the pouch from the protrusion, the opening completed without making any contact with a second object disposed within the pouch.

16. The method of claim 15, further comprising removing the object from within the pouch without making any contact with the object.

17. The method of claim 16, wherein opening the pouch includes separating the two parts of the pouch so that each part no longer faces the other.

* * * * *